(12) United States Patent
Yamashita et al.

(10) Patent No.: US 11,254,707 B2
(45) Date of Patent: Feb. 22, 2022

(54) PEPTIDE BINDING TO ARSENIC-CONTAINING MINERAL AND USE THEREOF

(71) Applicants: SHIBAURA INSTITUTE OF TECHNOLOGY, Tokyo (JP); JX NIPPON MINING & METALS CORPORATION, Tokyo (JP)

(72) Inventors: Mitsuo Yamashita, Tokyo (JP); Akira Miura, Hitachi (JP)

(73) Assignees: SHIBAURA INSTITUTE OF TECHNOLOGY, Tokyo (JP); JX NIPPON MINING & METALS CORPORATION, Tokyo (JP)

( * ) Notice: Subject to any disclaimer, the term of this patent is extended or adjusted under 35 U.S.C. 154(b) by 0 days.

(21) Appl. No.: 16/333,502

(22) PCT Filed: Sep. 15, 2017

(86) PCT No.: PCT/JP2017/033537
§ 371 (c)(1),
(2) Date: Mar. 14, 2019

(87) PCT Pub. No.: WO2018/052134
PCT Pub. Date: Mar. 22, 2018

(65) Prior Publication Data
US 2019/0345201 A1    Nov. 14, 2019

(30) Foreign Application Priority Data

Sep. 15, 2016  (JP) .............................. JP2016-180624
Mar. 2, 2017   (JP) .............................. JP2017-039617

(51) Int. Cl.
| | |
|---|---|
| *C07K 7/08* | (2006.01) |
| *B03D 1/016* | (2006.01) |
| *B03D 1/02* | (2006.01) |
| *C22B 1/11* | (2006.01) |
| *C22B 3/18* | (2006.01) |
| *C22B 30/04* | (2006.01) |

(52) U.S. Cl.
CPC ............... *C07K 7/08* (2013.01); *B03D 1/016* (2013.01); *B03D 1/023* (2013.01); *C22B 1/11* (2013.01); *C22B 3/18* (2013.01); *C22B 30/04* (2013.01); *B03D 2201/02* (2013.01); *B03D 2201/06* (2013.01); *B03D 2203/02* (2013.01)

(58) Field of Classification Search
None
See application file for complete search history.

(56) References Cited

U.S. PATENT DOCUMENTS

| | | |
|---|---|---|
| 2011/0094942 A1 | 4/2011 | Ochi et al. |
| 2013/0004389 A1 | 1/2013 | Okamoto et al. |

FOREIGN PATENT DOCUMENTS

| | | | |
|---|---|---|---|
| AU | 2011318944 B2 | | 4/2012 |
| JP | 2010-133004 A | | 6/2010 |
| JP | 2011-156521 A | | 8/2011 |
| JP | 2012-87400 A  | | 5/2012 |
| WO | WO 2015/142393 | * | 9/2015 |

OTHER PUBLICATIONS

NCBI Reference Sequence WP090630017.1; dehydrogenase [Parapedobacter indicus] (Year: 2017).*
International Preliminary Report on Patentability and English translation of the Written Opinion of the International Searching Authority for International Application No. PCT/JP2017/033537, dated Mar. 28, 2019.
Curtis et al., "Identification of Mineral-Binding Peptides That Discriminate Between Chalcopyrite and Enargite", Biotechnology and Bioengineering, vol. 114, No. 5, Nov. 28, 2016, pp. 998-1005.
Curtis et al., "Effects of Bacteriophage on the Surface Properties of Chalcopyrite (CuFeS2), and Phage-Induced Flocculation of Chalcopyrite, Glacial Till, and Oil Sands Tailings", Biotechnology and Bioengineering, vol. 108, No. 7, Feb. 17, 2011, pp. 1579-1590.
International Search Report for PCT/JP2017/033537 dated Nov. 7, 2017.

* cited by examiner

*Primary Examiner* — Sergio Coffa
(74) *Attorney, Agent, or Firm* — Birch, Stewart, Kolasch & Birch, LLP

(57) ABSTRACT

Providing a method for selecting minerals containing arsenic. A peptide comprising an amino acids sequence according to the following formula: (T, S, N, or Q)-(H, P, or W)-(E, or D)-(H, P, W, R, or K)-(L, I, V, F, or A)-(L, I, V, F, or A)-(L, I, V, F, or A)-(T, S, N, or Q)-(H, P, or W)-(L, I, V, F, or A)-(T, S, N, or Q)-(L, I, V, F, or A) wherein one amino acid is respectively selected from each group defined by paired parentheses.

11 Claims, 4 Drawing Sheets

Specification includes a Sequence Listing.

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Randomly synthesized peptide

<400> SEQUENCE: 1

Asn Pro Glu His Ala Ala Phe Ser Pro Val Thr Val
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Randomly synthesized peptide

<400> SEQUENCE: 2

Gly Gly Gly Asn Pro Glu His Ala Ala Phe Ser Pro Val Thr Val
1               5                   10                  15
```

PEPTIDE BINDING TO ARSENIC-CONTAINING MINERAL AND USE THEREOF

REFERENCE TO SEQUENCE LISTING SUBMITTED VIA EFS-WEB

This application includes an electronically submitted sequence listing in .txt format. The .txt file contains a sequence listing entitled "5526_0155PUS1_Sequence_Listing_ST25.txt" created on Oct. 14, 2020 and is 965 bytes in size. The sequence listing contained in this .txt file is part of the specification and is hereby incorporated by reference herein in its entirety.

TECHNICAL FIELD

The present invention is related to a novel peptide and use thereof. More particularly, the present invention is related to a novel peptide specifically binding to a certain mineral and use thereof.

BACKGROUND ART

Some mineral resources contain valuable metals while they may contain harmful substances. For example, a copper mineral that is mainly produced from copper mine is a sulfide mineral. This sulfide mineral may be roughly classified into a secondary sulfide minerals (which contains relatively high amount of copper, and mainly contains minerals such as chalcocite ($Cu_2S$) and covellite (CuS)) and a primary sulfide mineral (which contains relatively low amount of copper and mainly contains such as chalcopyrite ($CuFeS_2$)). In addition to these minerals, this sulfide mineral also includes arsenic-containing mineral (such as enargite).

Arsenic, which is harmful to environment, may cause various problems when refining sulfide minerals that are contaminated with arsenic-containing minerals. Therefore, arsenic is conventionally removed via various techniques prior to refining. For example, Japanese Patent Publication No 2012-087400 teaches roasting to evaporate arsenic for the purpose of removing arsenic from minerals in advance.

Japanese Patent Publication No 2010-133004 teaches using sodium thiosulfate as depressant for the purpose of isolating arsenic-containing minerals from minerals containing copper and arsenic.

Japanese Patent Publication No 2011-156521 teaches froth flotation with use of chelate as depressant (such as polyethyleneamine) for the purpose of removing arsenic from minerals containing copper and arsenic.

CITATION LIST

Patent Literature

[PTL 1] Japanese Patent Publication No 2012-087400
[PTL 2] Japanese Patent Publication No 2010-133004
[PTL 3] Japanese Patent Publication No 2011-156521

SUMMARY OF INVENTION

Technical Problem

In conventional method such as roasting to evaporate arsenic for removal as taught in Patent literature 1, a large scale of facility has been required. Furthermore, some minerals are difficult to be physically deprived of arsenic. Especially, it is quite often that copper minerals mainly containing such as chalcopyrite and bornite, and copper minerals mainly containing such as chalcocite also contains arsenic-containing minerals such as tennantite ($(CuFe)_{12}As_4S_{13}$) and enargite ($Cu_3AsS_4$). Furthermore, these minerals containing both of arsenic and copper has feature for froth flotation that is similar to those of chalcopyrite and bornite. Thus, it is difficult to separate via froth flotation arsenic-containing minerals from copper-containing minerals. Regarding to the methods using sodium thiosulfate according to Patent literature 2 or chelate according to Patent literature 3, separation of arsenic-containing minerals from copper-containing minerals is insufficient and these methods have not been practically used.

An object of the present invention is to provide novel methods for efficiently isolating arsenic-containing minerals.

Solution to Problem

In light of the above object, the present inventors have studied intensively and found that a certain peptide and phages having the certain peptide can selectively bind to arsenic-containing minerals.

On the basis of the above discovery, in one aspect, the present invention includes the following inventions.
(Invention 1)
A peptide comprising an amino acids sequence according to the following formula:
(T, S, N, or Q)-(H, P, or W)-(E, or D)-(H, P, W, R, or K)-(L, I, V, F, or A)-(L, I, V, F, or A)-(L, I, V, F, or A)-(T, S, N, or Q)-(H, P, or W)-(L, I, V, F, or A)-(T, S, N, or Q)-(L, I, V, F, or A),
wherein one amino acid is respectively selected from each group defined by paired parentheses.
(Invention 2)
A peptide comprising the following sequence:
Asn-Pro-Glu-His-Ala-Ala-Phe-Ser-Pro-Val-Thr-Val (SEQ ID NO: 1)
(Invention 3)
A peptide according to the following sequence:
Asn-Pro-Glu-His-Ala-Ala-Phe-Ser-Pro-Val-Thr-Val (SEQ ID NO: 1)
(Invention 4)
A peptide comprising a sequence which is at least 90% identical to the following sequence:
Asn-Pro-Glu-His-Ala-Ala-Phe-Ser-Pro-Val-Thr-Val (SEQ ID NO: 1)
(Invention 5)
A peptide comprising a sequence which is at least 95% identical to the following sequence:
Asn-Pro-Glu-His-Ala-Ala-Phe-Ser-Pro-Val-Thr-Val (SEQ ID NO: 1)
(Invention 6)
A peptide comprising a sequence which is at least 98% identical to the following sequence:
Asn-Pro-Glu-His-Ala-Ala-Phe-Ser-Pro-Val-Thr-Val (SEQ ID NO: 1)
(Invention 7)
A peptide comprising a sequence derived from the following sequence by deleting, replacing, and/or adding 1-5 amino acid:
Asn-Pro-Glu-His-Ala-Ala-Phe-Ser-Pro-Val-Thr-Val (SEQ ID NO: 1)

(Invention 8)

A composition for selecting and/or identifying a mineral containing arsenic, the composition comprising the peptide of any one of Inventions 1-7.

(Invention 9)

A nucleic acid encoding the peptide of any one of Inventions 1-7

(Invention 10)

A nucleic acid comprising a sequence which is at least 90% identical to a nucleic acid sequence encoding the peptide of any one of Inventions 1-7.

(Invention 11)

A nucleic acid being capable of hybridizing under a stringent condition with a sequence being complimentary to a nucleic acid encoding the peptide of any one of Inventions 1-7.

(Invention 12)

A microorganism comprising on its surface the peptide of any one of Inventions 1-7.

(Invention 13)

A microorganism comprising the nucleic acid of any one of Inventions 9-11.

(Invention 14)

A particle comprising on its surface the peptide of any one of Inventions 1-7.

(Invention 15)

A purification column comprising the peptide of any one of Inventions 1-7.

(Invention 16)

A collector for use of froth flotation comprising the peptide of any one of Inventions 1-7.

(Invention 17)

A depressant for use of froth flotation comprising the peptide of any one of Inventions 1-7.

(Invention 18)

A method for isolating a mineral containing arsenic, the method comprising using the peptide of any one of Inventions 1-7.

(Invention 19)

A method for selecting and/or identifying a mineral containing arsenic, the method comprising using the peptide of any one of Inventions 1-7 or the composition of Invention 8.

(Invention 20)

The method of Invention 19, the method comprising:
adding a microorganism into mineral dispersion, wherein the microorganism comprises the peptide on its surface and wherein the mineral contains arsenic;
aggregating and precipitating the mineral; and
recovering the aggregated and precipitated mineral.

(Invention 21)

The method of Invention 19, the method comprising:
affixing the peptide to a carrier;
introducing the carrier into a column for chromatography; and
passing mineral dispersion through the column, wherein the mineral contains arsenic.

(Invention 22)

The method of Invention 19, the method comprising:
affixing the peptide to a particle; and
introducing the particle into mineral dispersion, wherein the mineral contains arsenic.

(Invention 23)

The method of Invention 19, the method comprising froth floating with use of the peptide.

(Invention 24)

The method of Invention 23, the froth floating comprising:
introducing a mixture, the mixture containing:
the mineral containing arsenic; and
pyrite and/or chalcopyrite; and
introducing the peptide and/or the microorganism containing the peptide as depressant,
whereby the mineral containing arsenic is sorted to flotation tailings and the pyrite and/or chalcopyrite is sorted to concentrate.

(Invention 25)

The method of Invention 24, wherein the mineral containing arsenic is enargite and the microorganism is phage.

(Invention 26)

The method of any one of Inventions 18-25, wherein pH for dispersion of the mineral containing arsenic is 6 or more.

Advantageous Effects of Invention

In one aspect, the present invention utilizes a peptide. Thereby, it does not require a large scale of devices comparing to conventional techniques.

Furthermore, the peptides according to the present invention enable to isolate a mineral of interest efficiently. Moreover, a mineral of interest can be selectively isolated.

DESCRIPTION OF EMBODIMENTS

Now, for the purpose of enhancing the understanding of the present invention, more specified embodiments are described hereinafter, which are not intended to limit the scope of the present invention.

1. Applicable Substances

In one embodiment, the present invention is applicable to a method for isolating certain substances. The certain substances may include arsenic-containing minerals. More specifically, the certain substances may include minerals containing both of arsenic and copper. The minerals containing both of arsenic and copper may include enargite and tennantite.

2. Peptide

For the purpose of isolating the substances described above, in one embodiment of the present invention, a peptide can be used. More specifically, a peptide can be used that includes an amino acids sequence according to the following formula (1). Additionally, certain number of amino acid can be added in their N terminal and/or C terminal. The certain number may fall within numerical range defined by two numbers selected from 1, 2, 3, 4, 5, 6, 7, 8, 9, 10, 15, and 20 (e.g., from 1 to 10, or from 5 to 20).

(1) (T, S, N, or Q)-(H, P, or W)-(E, or D)-(H, P, W, R, or K)-(L, I, V, F, or A)-(L, I, V, F, or A)-(L, I, V, F, or A)-(T, S, N, or Q)-(H, P, or W)-(L, I, V, F, or A)-(T, S, N, or Q)-(L, I, V, F, or A)

(wherein one amino acid is respectively selected from each group defined by paired parentheses)

The working examples described hereinafter show the peptide according to the following amino acid sequence was used to isolate enargite.

(2) Asn-Pro-Glu-His-Ala-Ala-Phe-Ser-Pro-Val-Thr-Val (SEQ ID NO: 1)

The above amino acid sequence of (1) and the above amino acid sequence of (2) correspond to each other as follows.

TABLE 1

| | (2) | (1) |
|---|---|---|
| 1 | Asn | (T, S, N, or Q) |
| 2 | Pro | (H, P, or W) |
| 3 | Glu | (E, or D) |
| 4 | His | (H, P, W, R, or K) |
| 5 | Ala | (L, I, V, F, or A) |
| 6 | Ala | (L, I, V, F, or A) |
| 7 | Phe | (L, I, V, F, or A) |
| 8 | Ser | (T, S, N, or Q) |
| 9 | Pro | (H, P, or W) |
| 10 | Val | (L, I, V, F, or A) |
| 11 | Thr | (T, S, N, or Q) |
| 12 | Val | (L, I, V, F, or A) |

As shown in Table 1, the first amino acid in the sequence (2) is asparagine. This is a polar non-charged amino acid. Thus, even if replacing with threonine, serine, or glutamine, which are also polar non-charged amino acids, the peptide will retain same or similar property. Also, the eighth amino acid serine and the eleventh amino acid threonine in the sequence (2) can be replaced in a similar manner to retain same or similar property.

The second and ninth amino acids in the sequence (2) are proline, which has a ring compound containing nitrogen in its residue. Thus, even if replacing with histidine or tryptophan, which also have a ring compound containing nitrogen in their residue, the peptide will retain same or similar property. Also, the fourth amino acid histidine in the sequence (2) can be replaced in a similar manner to retain same or similar property.

The third amino acid in the sequence (2) is glutamic acid, which is an acidic amino acid. Thus, even if replacing with aspartic acid, which is also an acidic amino acid, the peptide will retain same or similar property.

The fourth amino acid in the sequence (2) is histidine, which has a ring compound containing nitrogen in its residue as described above. Furthermore, histidine is a basic amino acid. Thus, even if replacing with arginine or lysine, all of which are also a basic amino acid, the peptide will retain same or similar property.

The fifth amino acid in the sequence (2) is alanine, which has a hydrophobic residue. Thus, even if replacing with leucine, isoleucine, valine, or phenylalanine, all of which have also hydrophobic residue, the peptide will retain same or similar property. Also, the sixth amino acid alanine, the seventh amino acid phenylalanine, the tenth amino acid valine or the twelfth amino acid valine in the sequence (2) can be replaced in a similar manner to retain same or similar property.

In one embodiment, the present invention encompasses the peptides including the following sequence.

(2) Asn-Pro-Glu-His-Ala-Ala-Phe-Ser-Pro-Val-Thr-Val (SEQ ID NO: 1)

Additionally, an arbitrary number of amino acid can be added in its N terminal and/or C terminal. Typically, the arbitrary number may fall within numerical range defined by two numbers selected from 1, 2, 3, 4, 5, 6, 7, 8, 9, 10, 15, and 20 (e.g., from 1 to 10, or from 5 to 20).

In one embodiment, the present invention encompasses the peptides represented by the following 12-amino acid sequence.

(2) Asn-Pro-Glu-His-Ala-Ala-Phe-Ser-Pro-Val-Thr-Val (SEQ ID NO: 1)

Regarding to the above amino acid sequence (2), even if making a slight modification (e.g., insertion, replacement, and/or addition of amino acid), the modified peptide will retain property that is the same as or similar to that of amino acid sequence (2). For example, a peptide or a peptide including a sequence which is 66% or more, 75% or more, 83% or more, 90% or more, 95% or more, 98% or more, or 99% or more identical to the amino acids sequence (2), will also retain the same or similar property.

A numerical value for sequence similarity can be calculated by technique known in the art. For example, the value may be calculated based on a value derived by Blastp, which is used for homology search of amino acids (or protein) and is provided by BLAST (Trademark).

In one embodiment, the present invention encompasses a peptide comprising a sequence derived from the following sequence by deleting, replacing, and/or adding 1-5 amino acids, typically, by deleting, replacing, and/or adding 4 or less, 3 or less, or 2 or less amino acids.

(2) Asn-Pro-Glu-His-Ala-Ala-Phe-Ser-Pro-Val-Thr-Val (SEQ ID NO: 1)

In one embodiment, the present invention encompasses a composition containing the above peptides. In other words, not only the above peptides, but also a composition containing at least any one of the above peptides together with other ingredients can achieve the same or similar functions. The composition may contain arbitrary ingredients (e.g., buffer, NaCl, sugar, etc.) on the conditions that they do not deteriorate the functions of the above peptides.

3. Nucleic Acid Encoding Peptide

In one embodiment, the present invention encompasses a nucleic acid encoding at least any one of the above peptides. The nucleic acid may be DNA or RNA. In one embodiment, the present invention encompasses a nucleic acid having a sequence being complimentary to a sense strand encoding at least any one of the above peptides.

In one embodiment, the present invention encompasses a nucleic acid comprising a sequence which is at least 80% or more, 85% or more, 90% or more, 95% or more, or 98% or more identical to a nucleic acid sequence encoding at least any one of the above peptides. As similar to the case of amino acids sequence, a numerical value for sequence similarity can be calculated by technique known in the art. For example, the value may be calculated based on a value derived from a search result by Blastn, which is provided by BLAST.

Moreover, in one embodiment, the present invention encompasses a nucleic acid being capable of hybridizing with a sequence being complimentary to sense strand of a nucleic acid encoding at least any one of the above peptides. More specifically, the present invention encompasses the nucleic acid being capable of hybridization under a stringent condition. The stringent condition may be a condition known in the art. For example, it may be a condition that is disclosed in Japanese patent publication No. 2015-023831. More specifically, it may be judged through the following procedure: using a filter in which DNA is fixed; hybridization in the presence of 0.7-1.0 M of NaCl under the temperature 65 degree Celsius; and washing a filter at the temperature of 65 degree Celsius, by 0.1-2×SSC (saline-sodium citrate) solution (1×SSC solution contains 150 mM NaCl, 15 mM Sodium citrate).

Any of the above described nucleic acids are usable for preparing a peptide of interest through genetic engineering technique. For example, any one or more of the above described nucleic acids may be introduced into expression vector to express a peptide of interest in a large scale. Alternatively, a phage having a peptide of interest on its surface may be prepared through a phage display method described hereinafter.

4. Usage of Peptide and/or Nucleic Acid

The above described peptides and/or nucleic acids may be applicable in various ways.

4-1. Microorganism

For example, utilizing genetic engineering technique (e.g., introducing at least any one of the above nucleic acids into genome of a microorganism), the microorganism may produce a peptide of interest in a large scale. Alternatively, expressing a peptide of interest in a surface of a microorganism, a substance of interest may be isolated with use of the microorganism. The term "microorganism" described herein includes organism belonging to fungi, monera, or protist of five-kingdom system. Also, the term "microorganism" described herein includes virus, though it does not belong to organism in a strict classification. Typically, fungi, bacteria, or virus may be used. Preferably, a microorganism may be used in which genetic engineering procedure is established (e.g., yeast, *E. coli, lactobacillus*, a bacteriophage). In one embodiment, the present invention encompasses such microorganisms.

4-2. Particle

In one embodiment, the present invention encompasses a particle having a peptide on its surface. The peptide may be any one of the above described peptides. Moreover, an example for a particle may include beads (e.g., magnetic beads, glass beads, high-molecular beads, etc.), and a carrier, etc. A size of a particle is not limited, and may be adjusted depending on its usage. A peptide may be bound to a surface of a particle by technique known in the art.

In one embodiment of the present invention, a substance of interest may be isolated with use of a particle having at least any one of the above peptides on its surface. For example, via the method described hereinafter, a substance of interest may be bound to the peptides and precipitated to be isolated.

4-3. Column for Purification

A substance of interest may be isolated via column chromatography. Column chromatography relies on property where a column (or functional groups on inner surface of column) selectively binds to certain substance. In one embodiment of the present invention, the above described peptides can be affixed to a carrier and then the carrier may be introduced into a column. Utilizing such a column, a substance of interest may be isolated.

4-4. Collector or Frother for Froth Flotation

Froth flotation is a method for separation by trapping particles via bubble. In this method, a collector or a frother may be used. In one embodiment, a peptide of the present invention may be bound to a collector or a frother known in the art such that it may be prone to be trapped by bubble. Alternatively, such a peptide may be bound to chemical moiety that renders hydrophobicity (e.g., alkyl group, phenyl group, a hydrophobic amino acid etc.) thereby working as a collector such that it may be prone to be trapped by bubble. Thereby, a substance of interest may be trapped by bubble and consequently be isolated.

4-5. Depressant for Froth Flotation

In another embodiment, a peptide of the present invention can hydrophilize surface of certain minerals. Thereby, it enables to inhibit the certain minerals floating in process of froth flotation.

The peptide of the present invention therefore may be used as a depressant. In this regard, the peptide per se may be used, alternatively, the peptide bound to a certain microorganism may be used, and alternatively, the peptide bound to a certain chemical compound may be used.

5. Embodiment for Application (Methods for Isolation)

Now methods for the above application are described hereinafter.

5-1. Substances to be Isolated

The above described embodiments for application are related to isolating a certain substance. For example, the above described arsenic-containing mineral (e.g., enargite) may be isolated.

5-2. A Method with Use of a Microorganism

In one embodiment of the present invention, using a microorganism, a substance (specifically, arsenic-containing mineral, more specifically, enargite) may be isolated. Regarding to a microorganism, any of the above described microorganisms may be used. Typically, a bacteriophage may be used.

Regarding to procedure, initially, by technique of genetic engineering known in the art, a nucleic acid sequence encoding the above described peptides may be introduced into a microorganism, to express them on the surface of the microorganism. Then, the microorganism may be introduced into mineral dispersion (liquid in which mineral particles are dispersed).

An amount of introduction for a microorganism may be appropriately adjusted by considering certain conditions such as an amount of minerals dispersing in liquid. For example of a phage, in relative to 3 g/L of mineral particle, the amount of a phage may be $0.5 \times 10^8$ pfu/mL-$5 \times 10^8$ pfu/mL, more preferably, $0.6 \times 10^8$ pfu/mL-$1.5 \times 10^8$ pfu/mL. Alternatively, in relative to 10 g/L of mineral particles, the amount of a phage may be $0.5 \times 10^9$ pfu/mL-$5 \times 10^9$ pfu/mL, more preferably, $0.6 \times 10^9$ pfu/mL-$1.5 \times 10^9$ pfu/mL.

Alternatively, the ratio of an amount of a phage (pfu/mL)/an amount of minerals (g/L) may be $0.13 \times 10^8$-$5 \times 10^8$, more preferably $0.33 \times 10^8$-$1 \times 10^8$.

Introducing a microorganism and then leaving a microorganism for a while, peptides on the surface of the microorganism bind to mineral particles to be aggregated and then to be precipitated. After this, the precipitated minerals on the bottom may be recovered.

5-3. A Method for Isolating by Column Chromatography

In one embodiment of the present invention, via column chromatography, a substance (specifically, arsenic-containing mineral, more specifically, enargite) may be isolated. In this procedure, initially, at least any one of the above described peptides is affixed to a carrier by technique known in the art. Then, the carrier may be introduced into column for purification. After preparing the column, liquid in which a substance disperses is passed through the column. Then the substance binds to inside of the column, and/or elution of the substance is delayed. Thereby, the substance of interest may be isolated.

5-4. A Method for Isolating by a Particle

In one embodiment of the present invention, using a particle, a substance (specifically, arsenic-containing mineral, more specifically, enargite) may be isolated. Initially, the above described peptides may be affixed to the surface of the particle by technique known in the art. Then, the particle may be introduced into mineral dispersion (liquid in which mineral particles are dispersed). Introducing the peptide-bound particle and then leaving it for a while, peptides on the surface of the particle bind to mineral particles to be aggregated and then to be precipitated. After this, the precipitated mineral on the bottom may be recovered. Alternatively, a particle may be a magnetic bead, and without waiting precipitation, mineral particle may be recovered by magnetic power.

5-5. Method for Isolation Via Froth Flotation

In one embodiment, the method of the present invention may isolate, with use of a collector or a frother, certain substances (specifically, arsenic-containing minerals, more specifically, enargite). Specifically, a collector or a frother may be bound to the peptide of the present invention via technique known in the art. Then the bound collector or frother may be introduced into solution to be agitated (other agents may be introduced if required) to produce bubble. After that, mineral particles may be introduced to be trapped by bubble. Thereby, mineral particles may be recovered. Alternatively, such a peptide may be bound to chemical moiety that renders hydrophobicity (e.g. alkyl group, phenyl group, a hydrophobic amino acid, etc.) thereby working as a collector such that it may be prone to be trapped by bubble.

In another embodiment, a peptide of the present invention may be used as a depressant. A depressant described herein refers to an agent for inhibiting certain minerals from floating in process of froth flotation.

Moreover, the peptide of the present invention may be integrated with microorganisms for its usage. More specifically, the peptide of the present invention may be used such that it exits on surface of microorganisms. The microorganisms may include the ones as exemplified in the section of "4-1. Microorganism". One of preferable microorganisms is phage, more preferable is M13 bacteriophage.

Although the following descriptions do not intend to limit the scope of the present invention, a peptide of the present invention can hydrophilize surface of arsenic-containing minerals (e.g. enargite), thereby enabling to inhibit the arsenic-containing minerals from being trapped by bubble.

Thus, the present invention may be advantageous especially in separating from minerals that may be sorted to concentrate fraction (e.g., pyrite, chalcopyrite, etc.).

Although not limited to certain conditions, froth flotation may be typically performed under the following conditions.

Pulp density 50-600 (dry-g/L)
Time for froth flotation 5-30 min
pH for froth flotation from 5 to 10
Collector 5-100 g/t (gram per ton of subject minerals)
Frother 0.001-100 g/t (gram per ton of solution for froth flotation)

An amount of peptide is not limited to a particular amount and an effective amount in view of a depressant may be appropriately determined under the above described conditions for froth flotation. In case of using microorganism comprising peptides, not peptide per se, an amount of peptide corresponding to the above may be used. For example, an amount of phage may be from $10^{\wedge}1\ 3$ pfu/L to $10^{\wedge}1\ 7$ pfu/L (from $10^{\wedge}1\ 7$ pfu/T to $10^{\wedge}2\ 1$ pfu/T).

Collector is an agent being able to selectively adsorb to surface of minerals of interest thereby increasing hydrophobicity of its surface. Specific examples includes, but not limited to, collector which is commercially available for recovering sulfide copper minerals with higher priority, more specifically, xanthate, and thiocarbamate and so on and mixture thereof, yet more specifically, potassium amylxanthate etc. The amount of collector may be from 5 to 100 g/t. If the amount is less than 5 g/t, it is difficult to obtain floated minerals (concentrate fraction), which is undesirable. If the amount is more than 100 g/t, its effect reaches plateau and more amount will be meaningless. Meanwhile, in case where rough selection as a preliminary step (rougher circuit) is followed by refining minerals (cleaner circuit) which is via froth flotation with use of the peptide and/or microorganism including the peptide for separating arsenic-containing minerals from other minerals, it may be omitted to introduce a collector at the stage of refining minerals. This is because the collector already exists, originating from the rougher circuit.

A frother is an agent which is dissolved in solvent to stabilize bubble in solution. Specific example may include, but not limited to, methyl isobutyl carbinol (MIBC), pine oil, Aerofroth 70(CYTEC) etc. An amount of a frother may be from 0.001 to 100 g/t. If the amount is less than 0.001 g/t, it is difficult to obtain floated minerals, which is undesirable. If the amount is more than 100 g/t, its effect reaches plateau and more amount will be meaningless. Meanwhile, in case where rough selection as a preliminary step (rougher circuit) is followed by refining minerals (cleaner circuit) which is via froth flotation with use of the peptide and/or microorganism including the peptide for separating arsenic-containing minerals from other minerals, it may be omitted to introduce a frother at the stage of refining minerals. This is because the frother already exists, originating from the rougher circuit, as similar to a collector.

6. Selectivity for Binding to Mineral

The above described peptides have selectivity in that they strongly bind to specific minerals, but do not bind to other minerals. More specifically, they can strongly bind to arsenic-containing minerals (e.g., enargite), but do not bind to other minerals (such as elemental sulfur, chalcopyrite, pyrite) (alternatively, degree of their binding for arsenic-containing minerals is significantly higher than those of other minerals). Thus, from mixture of arsenic-containing minerals and other minerals, the above described methods enable to separate and/or remove arsenic-containing minerals. Alternatively, the above described peptide may be used for the purpose of identifying arsenic-containing minerals. For example, a detection marker (e.g., fluorescence molecule etc.) can be bound to peptides of the present invention to detect arsenic-containing minerals.

7. pH

A mineral containing arsenic (e.g., enargite) can be aggregated without any limitation of pH. For example, it can be typically aggregated within the range of pH 4-10, and it can be also aggregated within other pH ranges.

8. A Method for Preparing Peptide

The above described peptides may be prepared in various ways. DNA encoding at least any one of the above described peptides may be introduced into expression vector, and the vector may be introduced into a microorganism, etc., to express the peptides in a large scale to be recovered. Alternatively, in addition to genetic engineering technique, the peptides may be prepared via an organic chemistry technique.

Alternatively, in case of preparing a phage (e.g., M13-phage) having at least any one of the above described peptides on its surface, a phage display method may be available. A microorganism having a peptide of interest on its surface may be prepared by genetic engineering technique known in the art.

EXAMPLES

Now, via the following working examples, the above described embodiments of the present invention are described more specifically, although the scope of the present invention is not limited to the following working examples.

(Example 1) Selection of a Enargite-Adsorbing Phage Via a Phage Display Method For the purpose of screening peptides that are able to adsorb enargite, a phage display method was performed. Specifically, M13 bacteriophage library was constructed, in which peptides with 12 amino acids were randomly bound to phages. Using this library, enargite that was ground to the particle size of 75 micrometer or less was contacted with the library. Then, only bacteriophages that bound to enargite were recovered, and E. coli was infected with the recovered phages to grow the phages again. After that, the phages were contacted with enargite again, and only the adsorbed phages were recovered. These operations of adsorbing and recovering (panning) were repeated certain times. DNA sequences of the selected phages were analyzed to identify amino acids sequences binding to the phages.

At the screening, a pulp density of the contacted enargite was 3000 ppm and the panning was repeated 4 times. DNA sequences for the resultant phages were analyzed and the phages having peptide according to the following amino acid sequence were identified:

Asn-Pro-Glu-His-Ala-Ala-Phe-Ser-Pro-Val-Thr-Val (SEQ ID NO: 1)

Hereinafter, a phage being bound to the above peptide is referred to as A710-phage.

(Example 2) ELISA Analysis for Phages being Capable of Binding to Enargite

Using enargite and A710-phage that was screened in Example 1, an amount of binding to enargite were measured by ELISA method (Enzyme-Linked Immunosorbent Assay). Specifically, 3000 mg/L of enargite were suspended and then aliquoted to each well of 96-well microplate. Each phage was added into each well, and unbound phages were washed out. After that, anti M13-phage antibody conjugated with an enzyme (peroxidase) was added and then unbound anti-phage antibodies were washed out. Next, 2,2'-azino-bis (3-ethylbenzothiazoline-6-sulphonic acid) diammonium salt (ABTS), which is the substrate for the enzyme, was added. Blue-colored samples resulting from digestion of ABTS were analyzed by a microplate reader with the wave length of 405 nm. Furthermore, the same procedure was performed with the replacement with the other minerals (elemental sulfur, chalcopyrite, and pyrite).

Figure 1:
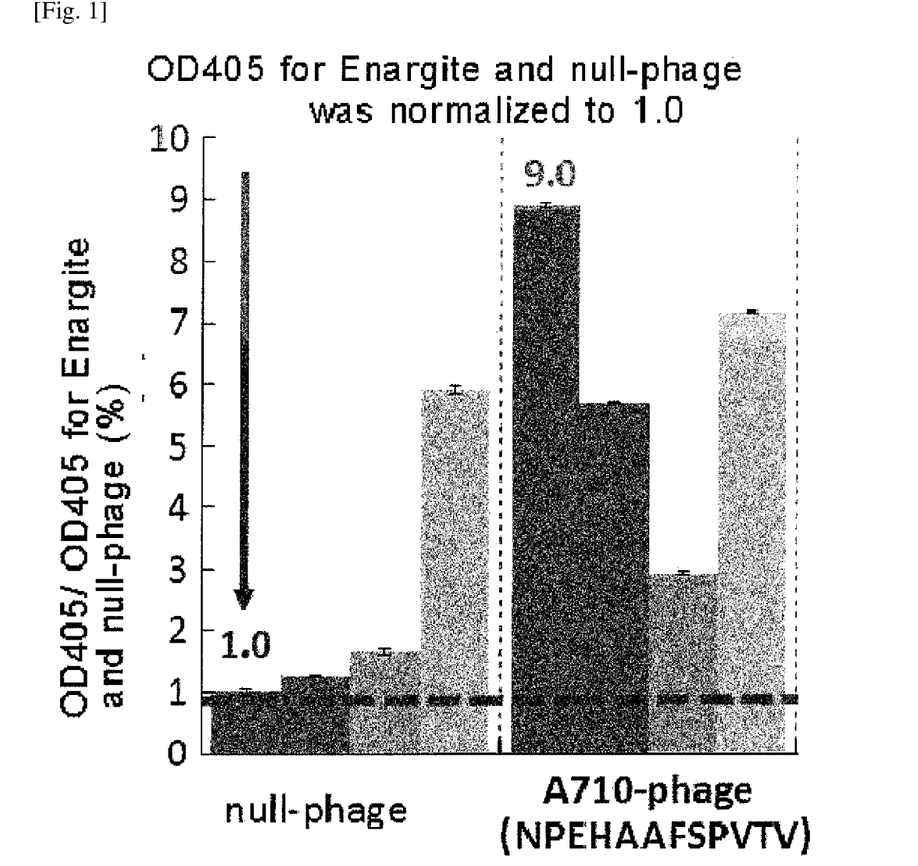
FIG. 1 (SEQ ID NO: 1) is a graph showing that the peptide according to one embodiment of the present invention can selectively bind to a certain mineral. Four bars in each group represent, in the order from left to right, OD405 for enargite, elemental sulfur, chalcopyrite, and pyrite with each phage respectively.

FIG. 1 shows a ratio of absorbance. Specifically, the absorbance of ELISA analysis under the conditions that M13-phage not having the peptides (null-phage) was contacted with enargite was deemed to be 100% (i.e., reference absorbance). On the basis of the reference absorbance, the ratio of the amounts of absorbance for each mineral and each phage having each peptide were calculated (that is, a ratio of the amount of binding by "phage having peptide" to each mineral to the amount of binding by "null-phage" to enargite). As shown in FIG. 1, the amount of binding by A710-phage to enargite was larger by 9 times in relative to the case where null-phage was contacted with enargite. Further, the amounts of binding by A710-phage to the other minerals (elemental sulfur, chalcopyrite, and pyrite) were significantly lower than that of enargite. Thus, it was shown that A710-phage specifically binds to enargite, and also shown that A710-phage is usable for screening enargite.

(Example 3) Observation by a Microscope in the Case of Enargite with a Density of 3 g/L

Figure 2:
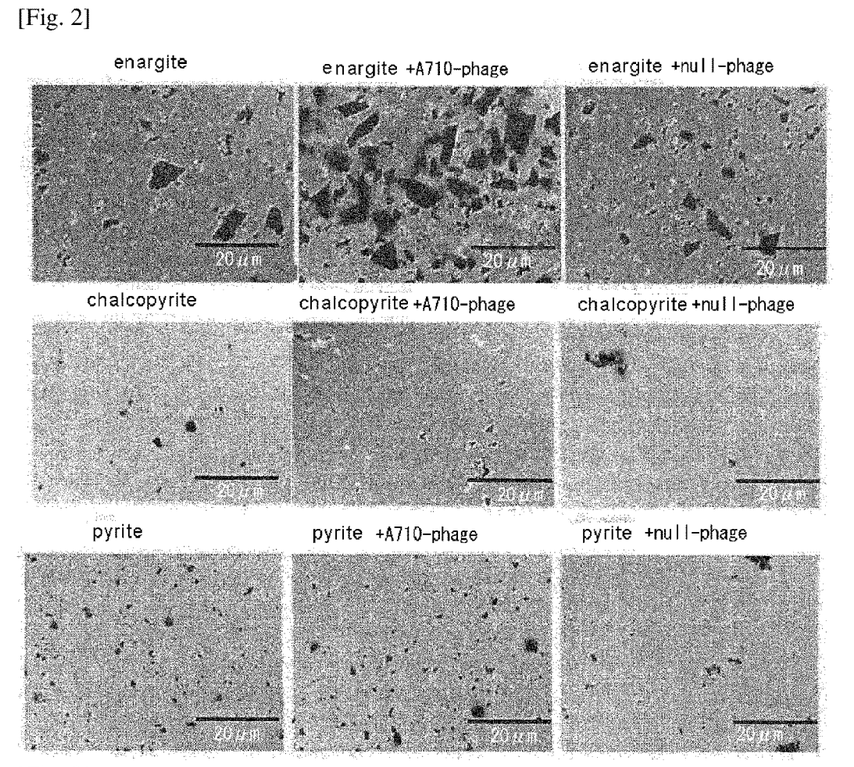
FIG. 2 is pictures showing that the size of particles changed when precipitating enargite, chalcopyrite, and pyrite with use of A710-phage etc. according to one embodiment of the present invention.

Under the conditions of the temperature of 30 degree Celsius, enargite with the particle size being 75 micrometer or less was suspended in water such that a pulp density was 3 g/L. Each of A710-phage and null-phage was added to the suspension such that each density was 10^7-10^9 pfu/ml. Then, the particles of enargite was observed by an optical microscope (FIG. 2), demonstrating that when A710-phage was added to enargite, the particles of enargite aggregated more significantly. Meanwhile, tests for other minerals (chalcopyrite, pyrite) were performed under the same conditions, resulting that any aggregation was not observed. These results indicate the possibility that enargite can be selectively isolated and recovered by adding A710-phage to suspension of enargite with an appropriate density.

(Example 4) Observation by a Microscope for Binding of a Synthesized Peptide with Enargite For the purpose of confirming more directly that a peptide according to the present invention can bind to certain mineral, the following synthesized peptide was prepared.

G  G  G  N  P  E

H  A  A  F  S  P  V  T  V

Specifically, solid-phase peptide synthesis (Fmoc method) was performed. Resin was used as solid-phase, and peptides were extended via dehydration condensation reaction. For the extension of peptide chain, Fmoc group (9-fluorenylmethyloxycarbonyl group) was used as protecting group, and enargite-binding peptide were prepared.

The fluorescent moiety was conjugated to N-terminal of the synthesized peptide.

Figure 3:
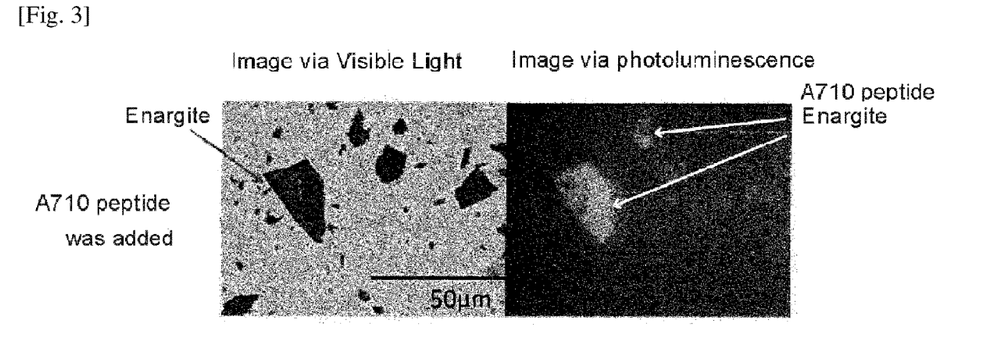
FIG. 3 is pictures showing that the synthesized peptides are able to bind to enargite.

Suspension of enargite was prepared. Specifically, enargite was ground such that its particle size was 75 micrometer or less, a density of enargite was adjusted to 10,000 mg/L. Further, pH of the suspension was adjusted to 7.0, and the above synthesized peptide was added such that the ultimate density was 0.1 ng/mL. After 5 minutes, the suspension was observed via a microscope with visible light, and then with fluorescein filters (excitation wavelength 450-490 nm, emission wavelength 510 nm). The results are shown in FIG. 3. Regarding to the observation via visible light, enargite was aggregated. Regarding to the observation via fluorescein filter, portions emitting fluorescence was consistent with portions where the aggregated enargite were observed via visible light. Thereby, it was shown that the peptides bind to enargite.

(Example 5) Bubble Pickup Test Using Peptide (Enargite)

A710-phages of Examples 1 and 2 were used for bubble pickup test. Specifically, enargite was initially suspended by pure water such that its density was 100 g/L and pH was adjusted to 7. Then, two types of sample were prepared. One was the suspension which A710-phage was introduced into (the ultimate density was 10^13 pfu/L). The other was the suspension without A710-phage. These samples were agitated by vortex mixer for one minute, and were left for five minutes.

Figure 4:
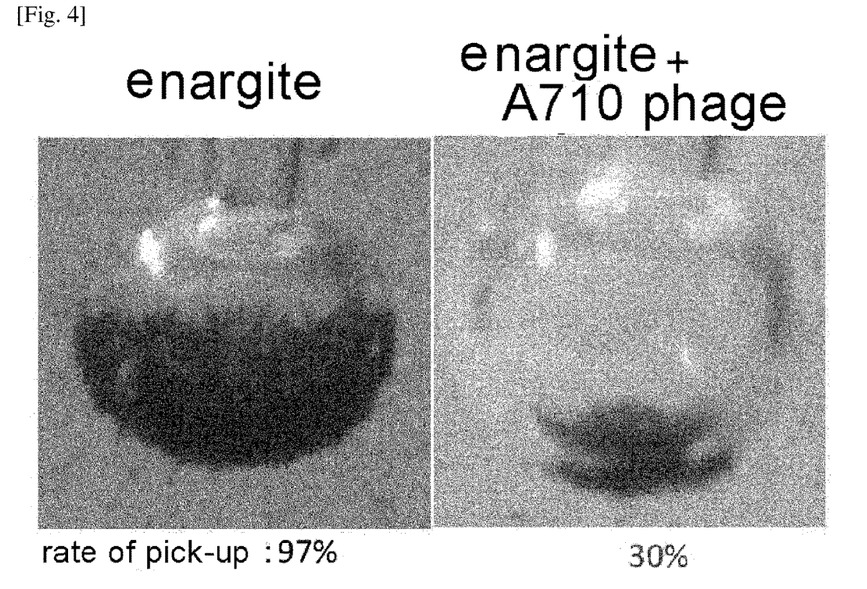
FIG. 4 shows results of Bubble pick-up test.

2 micro litter of bubble was formed on tip of micro pipette tip. Then, the bubble was contacted to the surfaces of the suspensions of the two samples for two seconds. The contacts were repeated 30 times. The probability of adhesion (rate of pickup) was calculated according to the following formula.

Rate of pickup (%)=(the number of times when minerals adhere/30)×100(%)

The results are shown in FIG. 4. It was shown that treating enargite by A710-phage significantly reduces adhesion to bubble.

(Example 6) Bubble Pickup Test Using Peptide (Pyrite and Chalcopyrite)

Figure 5:
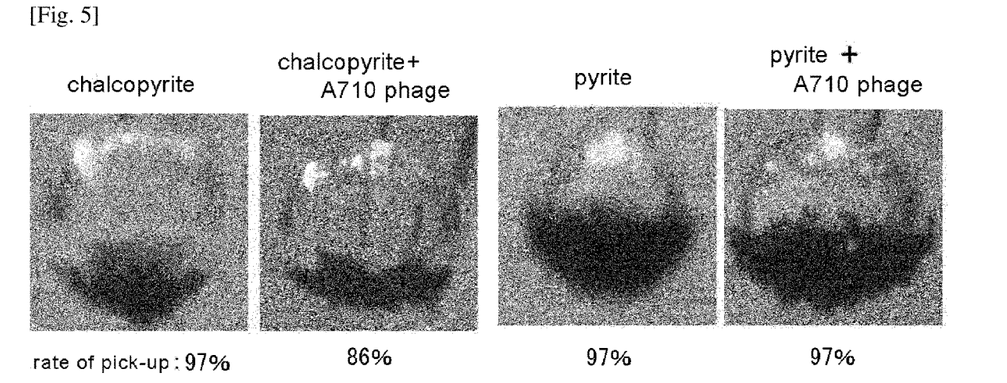
FIG. 5 shows results of Bubble pick-up test.

Tests were performed under the same conditions as that of Example 5, except for replacement of minerals with pyrite and chalcopyrite. The results are shown in FIG. 5. Any significant change for the rate of pickup depending on the presence or the absence of A710-phage was not observed.

The results of Examples 5 and 6 show that treating with A710 peptide can sort enargite into flotation tailings, not into froth fraction and can isolate from chalcopyrite and/or pyrite.

(Example 7) Froth Flotation Test Using Peptide (Enargite)

Froth flotation was performed under the following conditions.

Figure 6:
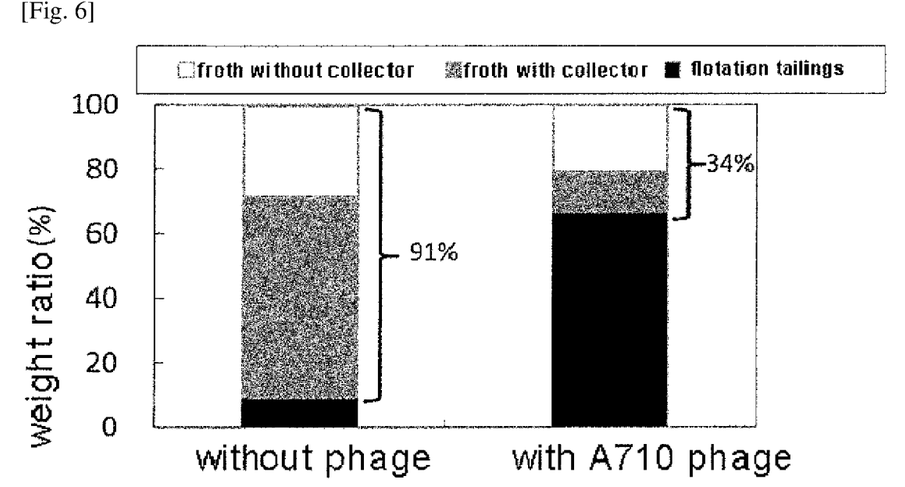
FIG. 6 shows results of froth flotation for enargite.

Enargite: 50 g/500 mL (Particle size from 25 micrometer to 75 micrometer),
Aeration: Air 1 L/min,
Agitation rate: 700 rpm,
pH: 5.6-6.3,
Frother: Aerofroth70 10 micro litter/L,
Phage to be added: A710 phage 10^13 pfu/L,
Collector: Potassium Amylxanthate 40 g/ton of mineral First, the minerals were introduced into tank. Then, (i) phage and frother, or (ii) frother were introduced and agitated for one minute. After that, aeration was started and froth was continuously skimmed until froth became white, in order to recover froth without collector. Next, aeration was stopped and collector was added to be agitated for one minute. Then, aeration was started again and froth was continuously skimmed until froth became white, in order to recover froth with collector. Finally, flotation tailings were recovered. The results are shown in FIG. 6. The results show that treating with A710 phage significantly increases the ratio that the minerals were sorted into flotation tailings.

(Example 8) Froth Flotation Test Using Peptide (Chalcopyrite)

Figure 7:
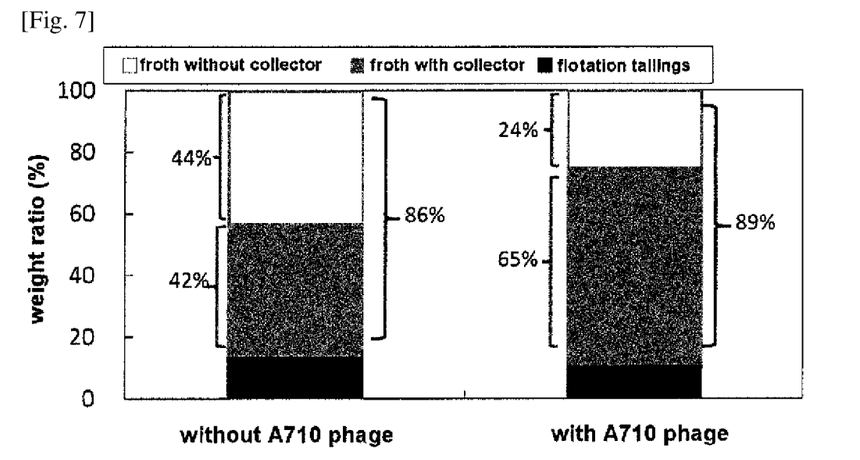
FIG. 7 shows results of froth flotation for chalcopyrite.

Froth flotation was performed under the following conditions.
Chalcopyrite: 50 g/500 mL (Particle size 75 micrometer or less),
Aeration: Air 1 L/min,
Agitation rate: 700 rpm,
pH: 5.6-6.3,
Frother: Aerofroth70 10 micro litter/L,
Phage to be added: A710 phage 10^13 pfu/L,
Collector: Potassium Amylxanthate 40 g/ton of mineral First, the minerals were introduced into tank. Then, (i) phage and frother, or (ii) frother was added and conditioning was performed for one minute. After that, aeration was started and scraping was continued until froth became white (froth without collector). Next, aeration was stopped and collector was added and conditioning was performed for one minute. Then, aeration was started again and scraping was continued until froth became white (froth with collector). Finally, flotation tailings were recovered. The results are shown in FIG. 7. Treating with A710 phage did not cause any significant change for the ratio of sorting into flotation tailings.

The invention claimed is:

1. A peptide comprising a sequence which is at least 90% identical to SEQ ID NO: 1.

2. The peptide of claim 1 comprising a sequence which is 100% identical to SEQ ID NO: 1.

3. A peptide comprising a sequence derived from SEQ ID NO: 1 by deleting, replacing, and/or adding 1 amino acid.

4. A method of selecting and/or identifying a mineral containing arsenic, comprising contacting said mineral with the peptide of claim 2.

5. A microorganism comprising on its surface the peptide of claim 1.

6. A particle comprising on its surface the peptide of claim 1.

7. A purification column comprising the peptide of claim 1.

8. A collector for froth flotation comprising the peptide of claim 1.

9. A depressant for froth flotation comprising the peptide of claim 1.

10. A method of selecting and/or identifying a mineral containing arsenic, the method comprising:
adding a microorganism into mineral dispersion, wherein the microorganism comprises the peptide of claim 1 on its surface and wherein the mineral contains arsenic;

aggregating and precipitating the mineral; and recovering the aggregated and precipitated mineral.

11. A method of selecting and/or identifying a mineral containing arsenic, the method comprising:

affixing the peptide of claim 2 to a carrier; introducing the carrier into a column for chromatography; and passing mineral dispersion through the column, wherein the mineral contains arsenic.

\* \* \* \* \*